United States Patent
Takeuchi et al.

(10) Patent No.: US 6,246,156 B1
(45) Date of Patent: Jun. 12, 2001

(54) PIEZOELECTRIC/ELECTROSTRICTIVE ELEMENT

(75) Inventors: Yukihisa Takeuchi, Aichi-prefecture; Koji Kimura, Nagoya, both of (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 09/276,580

(22) Filed: Mar. 25, 1999

(30) Foreign Application Priority Data

Mar. 27, 1998 (JP) .................................................. 10-082328
Mar. 31, 1998 (JP) .................................................. 10-087749

(51) Int. Cl.$^7$ .................................................. H01L 41/18
(52) U.S. Cl. .................................................. 310/328
(58) Field of Search .................................................. 310/328

(56) References Cited

U.S. PATENT DOCUMENTS

| | | | |
|---|---|---|---|
| 5,126,615 | * 6/1992 | Takeuchi | 310/330 |
| 5,210,455 | * 5/1993 | Takeuchi | 310/330 |
| 5,430,344 | * 7/1995 | Takeuchi | 310/330 |

FOREIGN PATENT DOCUMENTS

| | | |
|---|---|---|
| 0 526 048 A1 | 2/1993 | (EP) . |
| 0 671 772 A1 | 9/1995 | (EP) . |
| 3-128681 | 5/1991 | (JP) . |
| 5-29675 | 2/1993 | (JP) . |
| 5-49270 | 2/1993 | (JP) . |
| 5-97437 | 4/1993 | (JP) . |
| 5-270912 | 10/1993 | (JP) . |

OTHER PUBLICATIONS

Article entitled "Form foundation up to application Piezoelectric/Electrostrictive Actuator" written by Kenji Uchino edited by Japan Industrial Technique Center and published by Morikita Shuppan p. 177–178.

* cited by examiner

Primary Examiner—Elvin Enad
Assistant Examiner—Karen Addison
(74) Attorney, Agent, or Firm—Burr & Brown

(57) ABSTRACT

A piezoelectric/electrostrictive element has at least one film-type piezoelectric/electrostrictive operating portion constituted with a first electrode film, a piezoelectric/electrostrictive film, and a second electrode film on a ceramic substrate having a material whose main component is zirconium oxide. The ceramic substrate comprises a base layer and a surface layer, the crystal phase of the zirconium oxide of the base layer is a tetragonal phase or a mixed phase of tetragonal and cubic phase, tetragonal and monoclinic phase, or tetragonal, cubic, and monoclinic phase. The crystal phase of the zirconium oxide of the surface layer is mainly a cubic phase, and the piezoelectric/electrostrictive operating portion is formed on the surface layer. So it is possible to provide a high performance piezoelectric/electrostrictive element making sure of the strength of a ceramic substrate (diaphragm) and moreover, preventing a crack from occurring due to an internal factor in the firing process of a piezoelectric/electrostrictive film.

6 Claims, 3 Drawing Sheets

PIEZOELECTRIC/ELECTROSTRICTIVE ELEMENT

BACKGROUND OF THE INVENTION AND RELATED ART STATEMENT

The present invention relates to unimorph- and bimorph-type piezoelectric/electrostrictive elements used as various transducers and various actuators.

A piezoelectric/electrostrictive element is used in various fields such as various transducers for converting electrical energy into mechanical energy, that is, electrical energy into mechanical displacement, force, or vibration, and vice versa, various actuators, frequency-region functional components including various actuators and filters, various display devices including displays, sounding bodies including loudspeakers, microphones, and sensors including ultrasonic sensors.

For example, there are disclosed a piezoelectric/electrostrictive element comprising a film-type piezoelectric/electrostrictive operating portion 5 constituted with a ceramic substrate 1 serving as a diaphragm and a first electrode film 2, a piezoelectric/electrostrictive film 3, and a second electrode film 4 formed on the ceramic substrate 1 (Japanese Patent Application Laid-Open No. 3-128681) as shown in FIG. 1(*a*), and a piezoelectric/electrostrictive element in which a ceramic substrate has a cavity, the bottom of the cavity is constituted so as to be a thin-wall portion, and a piezoelectric/electrostrictive operating portion is integrated on the outer surface of the thin-wall portion (Japanese Patent Application Laid-Open No. 5-49270) as shown in FIG 1(*b*).

Moreover, a ceramic substrate using zirconium oxide partially stabilized with yttrium oxide is generally known as the ceramic substrate constituting a piezoelectric/electrostrictive element 7 (Japanese Patent Application Laid-Open Nos. 5-29675, 5-97437, and 5-270912).

In the case of the above piezoelectric/electrostrictive element, however, when forming a piezoelectric/electrostrictive operating portion 5 on the ceramic substrate 1 and firing the piezoelectric/electrostrictive operating-portion 5 in the fabrication process of the piezoelectric/electrostrictive element, a crack maybe recognized at a specific portion, that is, at a portion of ceramic-substrate 1 near the boundary of the first electrode film 2 as shown in FIGS. 2(*a*) and 2(*b*) particularly through heat treatment (firing) for integrating the piezoelectric/electrostrictive film 3 with the first electrode film 2 and the ceramic substrate 1 depending on the firing condition, and thereby a problem occurs that the production yield is lowered.

As a result of observing the vicinity of the portion where the crack occurs with an electron-probe microanalyzer (EPMA), it is found that the amount of yttrium oxide serving as a stabilizer for zirconium oxide is small as compared with other portions. Though the reason why the yttrium oxide is decreased is not known, it is estimated that, because the above portion is a portion which piezoelectric/electrostrictive film 3 directly contacts the ceramic substrate 1 when the piezoelectric/electrostrictive film 3 protrudes over the first electrode film 2 on the ceramic substrate 1 in order to prevent a short circuit from occurring between upper and lower electrodes, the yttrium oxide selectively diffuses to the piezoelectric/electrostrictive film 3 when the film 3 is sintered and integrated. Moreover, from the viewpoint of device structure, the vicinity of the boundary of the first electrode film 2 on the ceramic substrate 1 is a portion to which a large stress is easily applied to integrate the piezoelectric/electrostrictive film 3, first electrode film 5, and ceramic substrate 1 through heat treatment. Particularly, when the substrate has a cavity structure as shown in FIG. 1(*b*) or FIG. 2(*b*), it is estimated that the stress under the heat treatment causes a decrease in the yttrium oxide because the stress becomes high particularly in the cavity structure. However, this is not clear. In any case, however, it is strongly estimated that crystal phase transformation of zirconium oxide is induced due to a decrease in the yttrium oxide and this results in the crack formation.

To prevent a crack from occurring, it is considered to fabricate the ceramic substrate 1 with fully stabilized zirconium oxide in an attempt to prevent crystal phase transformation. However, fully stabilized zirconium oxide is inferior to partially stabilized zirconium oxide in mechanical strength. Therefore, for example, even when decreasing the thickness of the ceramic substrate 1 in order to improve the displacing characteristic of an actuator or the sensitivity of a sensor, a problem occurs that the thickness of the ceramic substrate 1 cannot be effectively or sufficiently decreased.

Therefore, though the partially stabilized zirconium oxide, particularly the zirconium oxide partially stabilized with 2 to 4 mol % of yttrium oxide, is superior in diaphragmatic characteristic, the partially stabillized zirconium oxide is susceptible to crystal phase transformation and cracking if the amount of yttrium oxide serving as a stabilizer is decreased due to any factor while sintering the piezoelectric/electrostrictive film 3 as described above. Moreover, the above problem is peculiar to a piezoelectric/electrostrictive element constituted by integrating a ceramic substrate serving as a diaphragm with a film-type piezoelectric/electrostrictive operating portion through heat treatment without using an adhesive or the like.

SUMMARY OF THE INVENTION

The present invention is made to solve the above problems and its object is to provide an advanced-functional and high-performance piezoelectric/electrostrictive element that uses the strength of a ceramic substrate (diaphragm) and preventing a crack from being produced due to an internal factor when firing a piezoelectric/electrostrictive film.

That is, the present invention provides a piezoelectric/electrostrictive-film-type element comprising: a ceramic substrate having a material whose main component is zirconium oxide and at least one film-type piezoelectric/electrostrictive operating portion comprising a first electrode film, a piezoelectric/electrostrictive film, and a second electrode film on the ceramic substrate; wherein the ceramic substrate comprises a base layer and a surface layer, and the crystal phase of the zirconium oxide of the base layer is a tetragonal phase or a mixed crystal phase of tetragonal and cubic phase, tetragonal and monoclinic phase, or tetragonal, cubic, and monoclinic phase, and the crystal phase of the zirconium oxide of the surface layer is mainly a cubic phase, and the piezoelectric/electrostrictive operating portion is formed on the surface layer.

In the piezoelectric/electrostrictive element of the present invention, it is preferable that the zirconium oxide of the surface layer is stabilizedwith 6 to 20 mol % of yttrium oxide. Moreover, it is preferable that the zirconium oxide of the base layer is partially stabilized with 2 to 4 mol % of yttrium oxide. Furthermore, it is preferable that the crystal grain size of the zirconium oxide in the base layer is held within a range of 0.1 and 1.5 μm.

Furthermore, in the piezoelectric/electrostrictive element of the present invention, it is preferable that only that portion of the ceramic substrate forming a piezoelectric/electrostrictive operating portion is thin-walled. As described later, in the present invention, the thickness of a ceramic substrate is preferably set to 50 μm or less. Therefore, it is possible to thicken the portion where the diaphram is not present, that is, where, a piezoelectric/electrostrictive operating portion is not formed, and thereby, advantageously handle the ceramic substrate. Moreover, even when arranging devices adjacent to one another, it is possible to set a thick wall portion between elements and this is advantageous in preventing mutual interference between characteristics of the elements.

DETAILED DESCRIPTION OF THE PREFERRED EMBODIMENT

Figure 3A:
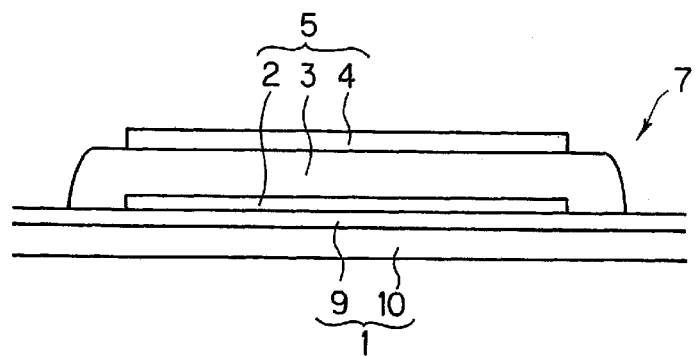
FIG. 3(a) is a schematic sectional view of a piezoelectric/electrostrictive element of the present invention and FIG. 3(b) a schematic sectional view of another piezoelectric/electrostrictive element of the present invention.
Figure 3B:
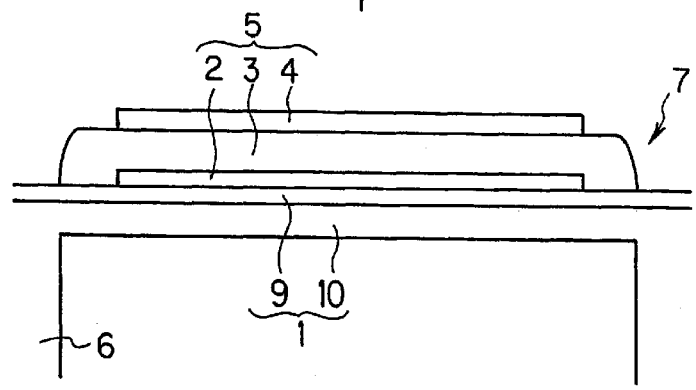

As shown in FIGS. 3(a) and 3(b), in a piezoelectric/electrostrictive element of the present invention, a ceramic substrate 1 having a material whose main component is zirconium oxide comprises a base layer 10 and a surface layer 9, and the surface layer 9, on which a piezoelectric/electrostrictive operating portion 5 is formed, mainly comprises zirconium oxide whose main crystal phase is cubic phase.

The cubic phase is a stable crystal phase and it does not easily cause phase transformation even if yttrium oxide decreases due to the firing environment of the piezoelectric/electrostrictive operating portion 5 or the stress or diffusion caused in firing the portion 5. Therefore, it is possible to effectively prevent a crack from occurring in the ceramic substrate 1 nearby the boundary of a first electrode film 2.

In a piezoelectric/electrostrictive element 7 of the present invention, a base layer 10 of a ceramic substrate 1 mainly comprises zirconium oxide which is a tetragonal phase or a mixed phase of tetragonal and cubic phase, tetragonal and monoclinic phase, or tetragonal, cubic, and monoclinic phase. Because the tetragonal phase or mixed phase of tetragonal and cubic phase, tetragonal and monoclinic phase, ortetragonal, cubic, and monoclinic phase is superior in toughness and strength, it is possible to provide a mechanical strength for the ceramic substrate 1. Therefore, a piezoelectric/electrostrictive element having excellent functional characteristic and productivity is realized. A main component in this application represents a component having a weight percentage of 85% or more.

In general, identification and ratio calculation of each crystal phase included in a crystal system is performed in accordance with the X-ray diffraction method or Raman spectroscopy. In the case of this application, the X-ray diffraction method is used to obtain the content ratio of each crystal phase in accordance with the intensity ratio between typical diffraction peaks of the crystal phases.

The content ratio of cubic phase is defined by the content ratio of the cubic phase to each crystal phase and the content of cubic phase is obtained in accordance with the intensity ratio between main diffraction peaks of the crystal phases. Moreover, the expression "mainly cubic phase" represents meeting the following relation.

$$\frac{I \cdot C(111)}{I \cdot M(\bar{1}11) + I \cdot C(111) + I \cdot T(111)} \geqq 0.70, \text{ preferably} \geqq 0.9$$

Moreover, when it is difficult to separate the main diffraction peaks of tetragonal and cubic phase from each other because the peaks are close to each other, it is also possible to use the intensity of a higher-order diffraction peak instead of the intensity of a main diffraction peak. In this case, however, it is necessary to standardize the intensity of the obtained higher-order diffraction peak in accordance with the intensity of the main diffraction peak by using the value of the intensities of a main diffraction peak and higher-order diffraction peak which are previously known through a JCPDS card or the like. For example, to obtain a content ratio by using the diffraction peaks of cubic phase (200) and tetragonal phase (002)+tetragonal phase (200), it is necessary to use the following expression instead of the above conditional expression because each diffraction-peak intensity is obtained as 25 and 43 (sum of (002) and (200)) to the main (111) diffraction-peak intensity 100 in accordance with the JCPDS card.

$$\frac{I \cdot [C+T](111)}{I \cdot M(\bar{1}11) + I \cdot [C+T](111)} \times$$

$$\frac{100/25 \times I \cdot C(200)}{100/25 \times I \cdot C(200) + 100/43 \times [I \cdot T(002) + I \cdot T(200)]}$$

$\geqq 0.70$, preferably $\geqq 0.9$

Each symbol in the above Equation has the following meaning.

I.M ($\bar{1}$11): Diffraction intensity of ($\bar{1}$11) of monoclinic phase

I.C (111): Diffraction intensity of (111) of cubic phase

I.T (111): Diffraction intensity of (111) of tetragonal phase

I·[C+T](111): Synthetic diffraction intensity of (111) of cubic phase and (111) of tetragonal phase I.T (002): Diffraction intensity of (002) of tetragonal phase I.C (200): Diffraction intensity of (200) of cubic phase I.T (200): Diffraction intensity of (200) of tetragonal phase In the piezoelectric/electrostrictive element 7 of the present invention, it is preferable that the total thickness (base layer+surface layer) of the ceramic substrate 1 is 50 μm or less, more preferably 30 μm or less, and further preferably 15 μm or less in order to maintain the quick-response characteristic of the piezoelectric/electrostrictive element and from the viewpoint of the amount of displacement, generation force, or sensitivity of the element. Moreover, in order to provide a sufficient strength for a piezoelectric/electrostrictive element and effectively prevent a crack from occurring, it is preferable that the ratio between the thicknesses of the base layer 10 and surface layer 9 is set to 6:4 to 8:2.

For the surface layer 9 to have a crystal phase that is mainly cubic phase, it is preferable to stabilize zirconium oxide in the surface layer by addition of 6 to 20 mol %, more preferably 7 to 10 mol % of yttrium oxide to the layer 9.

Moreover, for the base layer 10 to have a crystal phase a tetragonal phase or mixed phase of tetragonal and cubic phase, tetragonal and monoclinic phase, or tetragonal, cubic, and monoclinic phase, it is preferable to stabilize zirconium oxide in the base layer 10 by addition of 2 to 4 mol %, more preferably 2.5 to 3.5 mol % of yttrium oxide to the layer 10.

In the piezoelectric/electrostrictive element 7 of the present invention, it is preferable that the crystal grain size of the zirconium oxide of the base layer 10 is held within a range of 0.1 and 1.5 $\mu$m and more preferable that the size is 1.0 $\mu$m or less. By setting the crystal grain size to the above range, it is possible to obtain a large strength even for a small thickness and moreover, stably form a predetermined crystal phase.

It is possible to add aluminum oxide, titanium oxide, or a sintering aid such as clay to the ceramic substrate 1. However, if silicon oxide (SiO or $SiO_2$) is excessively contained in the base layer 10 or surface layer 9 after sintering, the reaction with a material constituting a piezoelectric/electrostrictive operating portion increases under heat treatment of the piezoelectric/electrostrictive operating portion and it is difficult to control the composition of the piezoelectric/electrostrictive operating portion, especially that of the piezoelectric/electrostrictive film. Therefore, it is necessary to set the content of silicon oxide to less than 1 wt %.

Figure 4:
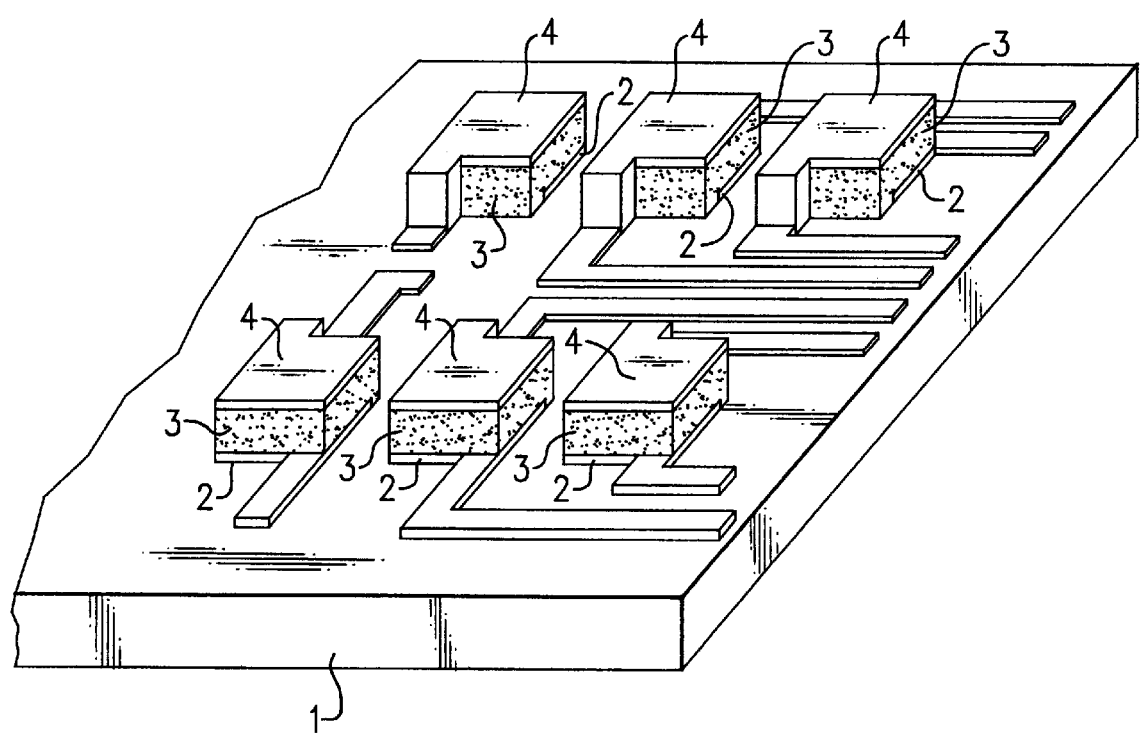
FIG. 4 is a perspective view of another piezoelectric/electrostrictive element of the present invention.

In the example of FIG. 4, a plurality of piezoelectric/electrostrictive elements (2, 3, 4) are formed on a relatively large ceramic substrate 1. In the case of FIG. 4, it is possible to use a ceramic substrate that only the portion forming a piezoelectric/electrostrictive operating portion is thin-walled.

A piezoelectric/electrostrictive element of the present invention may be manufactured as described below.

The ceramic substrate 1 is made by separately manufacturing green sheets for the base and surface layers that are composed of a predetermined material respectively by a doctor blade or reverse roll coater, superimposing them on each other while applying heat and pressure, and firing them at a temperature of 1,200 to 1,600° C. Moreover, it is possible to make the ceramic substrate 1 by forming a surface layer on a green sheet for the base layer through screen printing, spraying, or coating method by using a slurry or paste serving as a surface-layer material (it is also possible to form a surface layer only on the portion on which a piezoelectric/electrostrictive operating portion is formed) and similarly firing the ceramic substrate 1 or it is possible to make the ceramic substrate 1 by forming a base layer on a green sheet for the surface layer through screen printing, spraying, or coating method.

Moreover, to form a ceramic substrate into a structure having a cavity, a green sheet provided with one opening such as an aperture or cutout formed through its thickness serving as a cavity is prepared by using a die and a machining method such as ultrasonic machining in addition to the green sheet for the diaphragm (for the base and surface layers) to similarly superimpose both the green sheets on each other while applying heat and pressure and fire them. Furthermore, it is possible to form the ceramic substrate into a cavity structure provided with a member for closing an opening at an opposite side to the diaphragm.

The piezoelectric/electrostrictive operating portion 5 is formed on the ceramic substrate 1 by using a thick-film forming method such as screen printing, spraying, dipping, coating and electrophoresis, or a thin-film forming method such as ion-beam, sputtering, vacuum evaporation, ion plating, CVD, and plating. Particularly, one of the thick-film forming methods such as the screen printing, spraying, dipping, coating and electrophoresis method is preferably used to form a piezoelectric/electrostrictive film. According to these thick-film forming methods, it is possible to form a film on a ceramic substrate by using the paste, slurry, emulsion, suspension, or sol mainly containing ceramic particle of a piezoelectric/electrostrictive material having an average particle size of 0.01 to 5 $\mu$m, more preferably 0.05 to 3 $\mu$m, and thereby obtain a preferable device characteristic.

Moreover, to form the film into a desired shape, one of the following methods is used: a method for forming a pattern by using one of screen printing, photolithography, laser processing method such as excimer or YAG, and a method for forming a pattern by using a machining method such as ultrasonic machining or slicing and thereby removing unnecessary portions. Furthermore, as a temperature for heat-treating to integrate the film and ceramic substrate thus formed, within a range of 900 to 1,400° C., more preferably, within a range of 1,000 to 1,400° C. is advantageously selected.

Any material can be used for the first electrode film 2 constituting the piezoelectric/electrostrictive operating portion 5 as long as the material is a conductor capable of withstanding a high-temperature and an oxidation environment such as the above heat-treatment temperature and firing temperature. For example, it is also possible to use one of a single metal, an alloy, a mixture of insulating ceramics and a metal, or an alloy and conductive ceramics for the first electrode film 2. Particularly, it is preferable to use one of noble metals having a high melting point such as platinum, palladium, and rhodium, an electrode material mainly containing an alloy of silver and palladium, silver and platinum or platinum and palladium, cermet made of platinum and a ceramic substrate material, cermet made of platinum and a piezoelectric material, and cermet made of platinum, a substrate material, and a piezoelectric material. Among the above materials, it is more preferable to use a material containing platinum as a main component.

Moreover, when using glass such as silicon oxide as a material to be added to an electrode, a reaction easily occurs during heat treatment of a piezoelectric/electrostrictive layer, easily causing a device characteristic to deteriorate. Therefore, it is preferable to avoid using the glass. Furthermore, in the case of adding a substrate material to an electrode, it is preferable to add within a range of 5 to 30% by volume, and in the case of adding a piezoelectric/electrostrictive material, it is preferable to add within a range of 5 to 20% by volume.

The material of the second electrode film 4 is not restricted. It is possible to use one of the materials used as the first electrode film 2, gold, chromium, copper or the like formed by sputtering, or gold or silver film using resinate material.

As the material of the piezoelectric/electrostrictive film 3 constituting the piezoelectric/electrostrictive operating portion 5, it is possible to use any material as long as the material shows an electric field induced strain such as a piezoelectric or electrostrictive effect. For example, the piezoelectric/electrostrictive material maybe either a crystalline material or an amorphous material, and may be a semi-conductor material or a dielectric, ferroelectric ceramic or anti-ferroelectric ceramic material. Further, the piezoelectric/electrostrictive material may either require a treatment for initial polarization or poling, or may not require such a polarization treatment.

As piezoelectric/electrostrictive materials used for the present invention, the following materials are specifically listed: a material whose main component is lead zirconate titanate (PZT), lead titanate, lead zirconate, lead magnesium niobate (PMN), lead nickel niobate (PNN), lead magnesium tungstate, lead manganese niobate, lead antimony stannate, lead zinc niobate, lead magnesium tantalate, lead nickel tantalate, and a composite material of the above materials.

Moreover, it is possible to add the oxides of lanthanum, barium, niobium, zinc, cerium, cadmium, chromium, cobalt, antimony, iron, yttrium, tantalum, tungsten, nickel, manganese, lithium, strontium, magnesium, calcium, bismuth, tin, and a compound of these substances to above mentioned materials. Moreover, it is possible to use a PLZT-based material obtained by addition of the oxide of lanthanum to a PZT-based material.

It is better to avoid addition of glass such as silicon oxide because addition of the glass easily causes a reaction with a piezoelectric/electrostrictive material and it is difficult to keep a predetermined material composition.

Moreover, among the above piezoelectric/electrostrictive materials, it is preferable to use a material whose main component is a mixture of lead magnesium niobate, lead zirconate, and lead titanate, a material whose main component is a mixture of lead nickel niobate, lead magnesium niobate, lead zirconate, and lead titanate, a material whose main component is the mixture of lead nickel tantalate, lead magnesium niobate, lead zirconate, and lead titanate, or a material whose main component is a mixture of lead magnesium tantalate, lead magnesium niobate, lead zirconate, and lead titanate.

Furthermore, among the above materials, in particular, a material whose main component is the mixture of lead magnesium niobate, lead zirconate, and lead titanate is preferably used. Because this material not only has a high piezoelectric constant but is also particularly less relative with a substrate material during heat treatment.

In the case of a multicomponent piezoelectric/electrostrictive material, the piezoelectric/electrostrictive characteristics are changed depending on the composition of a component. However, in the case of a ternary system material made of lead magnesium-niobate, lead zirconate, and lead titanate preferably used for a piezoelectric/electrostrictive element of the present invention, a composition nearby the phase boundary between pseudo-cubicphase, tetragonal phase, and rhombohedral phase is preferable. Particularly, a composition containing 15 to 50 mol % of lead magnesium niobate, 10 to 45 mol % of lead zirconate, and 30 to 45 mol % of lead titanate is preferably used because the composition has a high piezoelectric constant and a high electromechanical coupling factor.

A piezoelectric/electrostrictive element of the present invention is preferably used for various transducers for converting electrical energy into mechanical energy, that is, a mechanical displacement, force, or vibration, and vice versa, various actuators, frequency-region functional parts including filters, various indication devices including displays, transformers, sounding bodies including microphones and loudspeakers, vibrators, resonators, or oscillators for communication or motive power, discriminators, various sensors including ultrasonic sensors, acceleration sensors, angular velocity sensors, impact sensors, and mass sensors, gyros, and moreover a unimorph-type device and a bimorph-type device used for the servo shift device, pulse driven motor, ultrasonic motor, piezoelectric fan, and piezoelectric relay described in "From foundation to application of piezoelectric/electrostrictive actuator" written by K. Uchino, (Edited by NIPPON KOGYOGIJUTSU CENTER), (MORIKITA SHUPPAN)", and more preferably used for various actuators, vibrators, sounding bodies, and display devices.

Moreover, a piezoelectric/electrostrictive element of the present invention can be used as a film-type capacitor device because it has not only the piezoelectric/electrostrictive characteristic but also dielectricity.

A piezoelectric/electrostrictive element of the present invention is described above on the basis of a unimorph structure constituting a piezoelectric/electrostrictive operating portion at only one side of a ceramic substrate. It is a matter of course that a piezoelectric/electrostrictive element of the present invention can be also applied to a bimorph structure constituting the piezoelectric/electrostrictive operating portion at both sides of the ceramic substrate. In this case, the surface layers are formed on both sides of the base layer.

EXAMPLES

The present invention is in more detail described below by using examples. However, the present invention is not restricted to these examples.

Example 1

A piezoelectric/electrostrictive element 7 shown in FIG. 3(b) was manufactured in which a ceramic substrate was constituted with a base layer and a surface layer and had a cavity. The base layer 10 was made of zirconium oxide which crystal phase was tetragonal phase obtained by addition of 3 mol % of yttrium oxide and the surface layer 9 was made of zirconium oxide obtained by addition of 7 mol % of yttrium oxide. The value of a conditional expression is 0.90. A piezoelectric/electrostrictive operating portion 5 was formed on the surface layer 9.

First, a surface layer was formed on the surface of a green sheet for the base layer by using a paste material for the surface layer by means of screen printing. The green sheet for the base layer and the surface layer were set so that the thickness of the base layer became 6 $\mu$m and that of the surface layer became 2 $\mu$m after they were fired.

Then, one opening was formed on a green sheet for a supporting member in order to form a cavity of 0.2 mm×4 mm and then, the green sheet for the supporting member and the green sheet for the base layer were superimposed under applying heat and pressure, and fired at 1,500° C.

Then, the piezoelectric/electrostrictive operating portion 5 was formed on the substrate. A first electrode film 2 was made of platinum, a piezoelectric/electrostrictive film 3 was made of a material whose main component is a mixture of lead zirconate, lead titanate, and lead magnesium niobate, and a second electrode film 4 was made of gold. Moreover, the piezoelectric/electrostrictive operating portion 5 was formed by means of screen printing. The first electrode film 2 was fired at 1,300° C., the piezoelectric/electrostrictive film 3 was fired at 1,250° C., and the second electrode film 4 was fired at 600° C. The thickness of the first electrode film 2 was set to 3 $\mu$m, that of the piezoelectric/electrostrictive film 3 was set to 14 $\mu$m, and that of the second electrode film 4 was set to 0.5 $\mu$m.

One thousand piezoelectric/electrostrictive elements 7 were manufactured to evaluate whether a crack occurred in a ceramic substrate 1 by using a crack-inspection penetrant. Table 1 shows a result of the evaluation.

Example 2

Zirconium oxide obtained by addition of 10 mol % of yttrium oxide to a surface layer 9 was used. One thousand piezoelectric/electrostrictive elements were manufactured by the same manner as the case of Example 1 except that the value of a conditional expression was 1 to evaluate whether a crack occurred in a ceramic substrate 1 in the same manner as the case of Example 1. Table 1 shows a result of the evaluation.

Example 3

Zirconium oxide obtained by addition of 6 mol % of yttrium oxide to a surface layer 9 was used. One thousand piezoelectric/electrostrictive elements were manufactured by the same manner as the case of Example 1 except that the value of a conditional expression was 0.80 to evaluate whether a crack occurred in a ceramic substrate 1 in the same manner as the case of Example 1. Table 1 shows a result of the evaluation.

Comparative Example 1

Figure 1A:
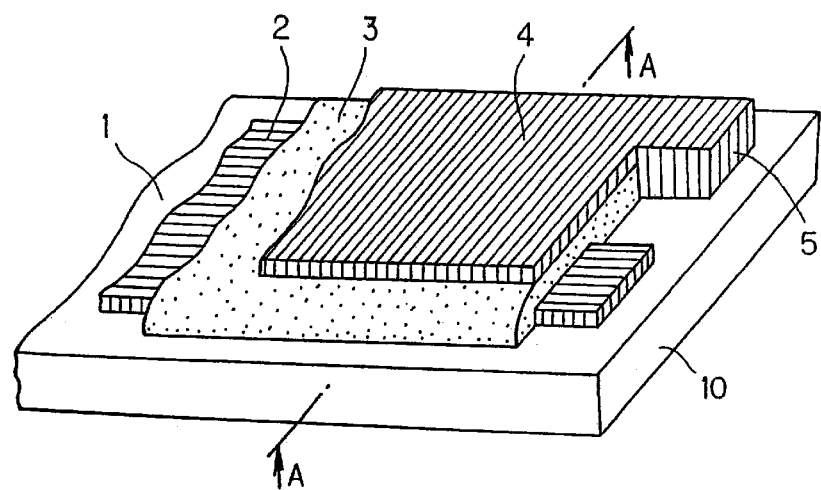
FIG. 1(a) is a perspective view of a conventional piezoelectric/electrostrictive element and FIG. 1(b) is a perspective view of another conventional piezoelectric/electrostrictive element.
Figure 1B:
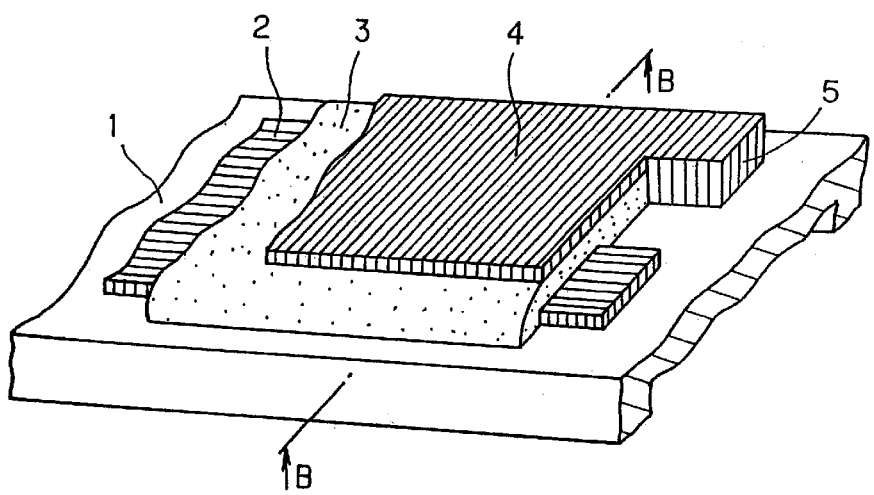
Figure 2A:
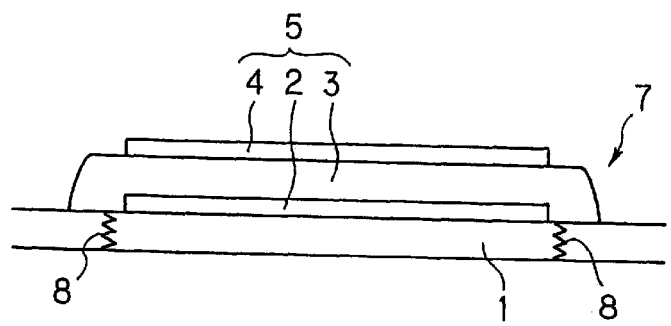
FIG. 2(a) is a sectional view of the crack occurrence portion of FIG. 1(a), taken along the line A—A of FIG. 1(a)
Figure 2B:
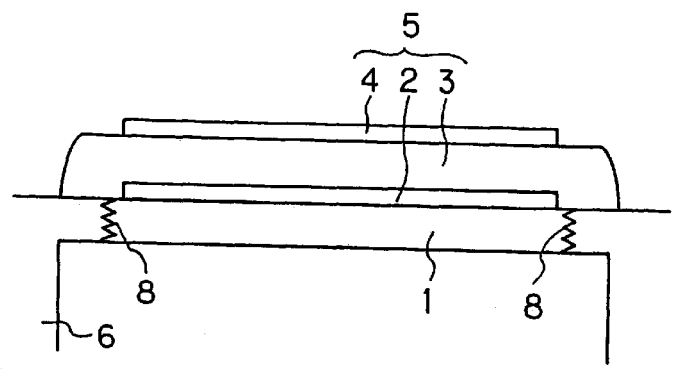
FIG. 2(b) is a sectional view of the crack occurrence portion of FIG. 1(b), taken along the line B—B of FIG. 1(b).

A piezoelectric/electrostrictive element 7 shown in FIG. 1(b) was manufactured in which a ceramic substrate was constituted with a single layer and had a cavity. The ceramic substrate was made of zirconium oxide which crystal phase was tetragonal phase obtained by addition of 3 mol % of yttrium oxide. A piezoelectric/electrostrictive operating portion 5 was formed on the surface of the ceramic substrate 1 at the opposite side to the side with which a support member 6 was connected.

An opening was formed on a green sheet for a supporting member in order to form a cavity of 0.2 mm×4 mm and then, the green sheet for the supporting member and a green sheet for the ceramic substrate were superimposed on each other while applying heat and pressure, and fired at 1,500° C. The thickness of a ceramic substrate after firing was set to 8 $\mu$m.

Then, a piezoelectric/electrostrictive operating portion 5 was formed on the ceramic substrate. The material and the thickness of each layer of the piezoelectric/electrostrictive operating portion 5 were the same as those of Example 1.

One thousand piezoelectric/electrostrictive elements 7 were manufactured to evaluate whether a crack occurred in the ceramic substrate 1 in the same manner as the case of Example 1. Table 1 shows a result of the evaluation.

From Table 1, it is found that the rates of crack occurrence of the piezoelectric/electrostrictive elements of the embodiments are effectively low compared to the rate of crack occurrence of the piezoelectric/electrostrictive element of Comparative Example 1.

In a piezoelectric/electrostrictive element of the present invention, a ceramic substrate comprises a base layer and a surface layer and the surface layer of the ceramic substrate on which the piezoelectric/electrostrictive operating portion is formed is made of the material whose main component is zirconium oxide which crystal phase is mainly cubic phase Therefore, a crack does not easily occur in the ceramic substrate nearby the boundary of a first electrode film. Moreover, because the base layer of the ceramic substrate is made of a material whose main component is zirconium oxide which crystal phase is a tetragonal phase or a mixed phase of tetragonal and cubic phase, tetragonal and monoclinic phase, or tetragonal, cubic, and monoclinic phase, it is possible to keep a high mechanical strength even with a small thickness. Therefore, it is possible to completely show the excellent characteristics in the function as a substrate (diaphragm) for a film type piezoelectric/electrostrictive element and provide a high performance piezoelectric/electrostrictive element.

TABLE 1

|  | Rate of crack occurrence (%) |
| --- | --- |
| Example 1 | 0.0 |
| Example 2 | 0.0 |
| Example 3 | 0.5 |
| Comparative example 1 | 1.0 |

What is claimed is:

1. A piezoelectric/electrostrictive element comprising;

a ceramic substrate having a material whose main component is zirconium oxide; and at least one film-type piezoelectric/electrostrictive operating portion comprising a first electrode film, a piezoelectric/electrostrictive film, and a second electrode film on the ceramic substrate;

wherein the ceramic substrate comprises a base layer and a surface layer, and the crystal phase of the zirconium oxide of the base layer is a tetragonal phase or a mixed phase of tetragonal and cubic phase, tetragonal and monoclinic phase, or tetragonal, cubic, and monoclinic phase, and the crystal phase of the zirconium oxide of the surface layer is mainly cubic phase, and the piezoelectric/electrostrictive operating portion is formed on the surface layer.

2. The piezoelectric/electrostrictive element according to claim 1, wherein the zirconium oxide in the surface layer is stabilized with 6 to 20 mol % of yttrium oxide.

3. The piezoelectric/electrostrictive element according to claim 1, wherein the zirconium oxide in the base layer is stabilized with 2 to 4 mol % of yttrium oxide.

4. The piezoelectric/electrostrictive element according to claim 1, wherein the crystal grain size of the zirconium oxide in the base layer is within a range of 0.1 and 1.5 $\mu$m.

5. The piezoelectric/electrostrictive element according to claim 1, wherein a supporting member having at least one opening is connected to the ceramic substrate so as to close one side of the opening with the ceramic substrate.

6. A piezoelectric/electrostrictive element comprising:

a ceramic substrate having a material whose main component is zirconium oxide;

at least one film-type piezoelectric/electrostrictive operating portion comprising a first electrode film, a piezoelectric/electrostrictive film, and a second electrode film on the ceramic substrate; and a supporting member having at least one opening, said supporting member being connected to the ceramic substrate so as to close one side of the opening with the ceramic substrate;

wherein the ceramic substrate comprises a base layer and a surface layer, and the crystal phase of the zirconium oxide of the base layer is a tetragonal phase or a mixed phase of tetragonal and cubic phase, tetragonal and monoclinic phase, or tetragonal, cubic, and monoclinic phase, and the zirconium oxide in the base layer is stabilized with 2 to 4 mol % of yttrium oxide, and the crystal grain size of the zirconium oxide in the base layer is within a range of 0.1 and 1.5 $\mu$m, and the crystal phase of the zirconium oxide of the surface layer is mainly cubic phase, and the piezoelectric/electrostrictive operating portion is formed on the surface layer.

* * * * *